(12) United States Patent
Delache et al.

(10) Patent No.: US 7,438,073 B2
(45) Date of Patent: Oct. 21, 2008

(54) AIR ASSISTANCE APPARATUS FOR COMPUTING THE AIRFLOW PROVIDED BY ONLY MEANS OF PRESSURE SENSORS

(75) Inventors: Alain Delache, Nice (FR); Véronique Delache, Nice (FR)

(73) Assignee: Kaerys S.A., Nice (FR)

( * ) Notice: Subject to any disclaimer, the term of this patent is extended or adjusted under 35 U.S.C. 154(b) by 280 days.

(21) Appl. No.: 10/506,980

(22) PCT Filed: Mar. 10, 2003

(86) PCT No.: PCT/IB03/01403

§ 371 (c)(1),
(2), (4) Date: Sep. 8, 2004

(87) PCT Pub. No.: WO03/075990

PCT Pub. Date: Sep. 18, 2003

(65) Prior Publication Data

US 2006/0162728 A1    Jul. 27, 2006

Related U.S. Application Data

(60) Provisional application No. 60/362,441, filed on Mar. 8, 2002.

(51) Int. Cl.
*A61M 16/00* (2006.01)
*A62B 7/00* (2006.01)
*F16K 31/02* (2006.01)

(52) U.S. Cl. ............................... 128/204.23

(58) Field of Classification Search ............ 128/204.18, 128/204.21, 204.23, 205.11, 205.18, 205.23, 128/204.26; 600/533, 538, 529; 73/1.57, 73/1.59

See application file for complete search history.

(56) References Cited

U.S. PATENT DOCUMENTS

| 5,233,998 A | * | 8/1993 | Chowienczyk et al. | ...... 600/533 |
| 5,245,995 A | | 9/1993 | Sullivan et al. | ........ 128/204.23 |
| 5,503,146 A | | 4/1996 | Froehlich et al. | ....... 128/204.23 |

(Continued)

FOREIGN PATENT DOCUMENTS

EP          0 821 976          2/1998

(Continued)

*Primary Examiner*—Justine R Yu
*Assistant Examiner*—Kristen C Matter
(74) *Attorney, Agent, or Firm*—Westerman, Hattori, Daniels & Adrian, LLP.

(57) ABSTRACT

An apparatus (1) to assist a patient's respiration by delivering air to a patient through a mask, the mask designed to be connected to a first extremity of a tube, the apparatus including: a control unit (2) to adjust the pressure delivered by a blower (4), a first pressure sensor (6) for sensing pressure PM at the first tube extremity and being connected to the control unit, and a second pressure sensor (8) for sensing pressure PB at the air output of the blower and being connected to the control unit; so that, when a tube is connected to the mask and connected to the apparatus at its second extremity, the air flowing from the apparatus to the mask, the control unit is able to calculate the airflow at the tube's second extremity from the pressures PM and PB and from the tube's airflow resistance coefficient $K_r$.

41 Claims, 9 Drawing Sheets

U.S. PATENT DOCUMENTS

| | | | | |
|---|---|---|---|---|
| 5,551,418 A | * | 9/1996 | Estes et al. | 128/204.23 |
| 5,970,975 A | | 10/1999 | Estes et al. | 128/204.23 |
| 5,977,737 A | | 11/1999 | Labriola, II | 318/599 |
| 6,066,101 A | * | 5/2000 | Johnson et al. | 600/533 |
| 6,152,129 A | * | 11/2000 | Berthon-Jones | 128/200.24 |
| 6,237,592 B1 | * | 5/2001 | Surjadi et al. | 128/204.21 |
| 6,287,264 B1 | * | 9/2001 | Hoffman | 600/538 |
| 6,400,131 B1 | * | 6/2002 | Turner | 324/130 |
| 2002/0000228 A1 | | 1/2002 | Schoeb | 128/204.19 |
| 2002/0014239 A1 | | 2/2002 | Chalvignac | 128/18 |
| 2002/0174729 A1 | * | 11/2002 | Danninger | 73/861.63 |
| 2004/0102914 A1 | * | 5/2004 | More | 702/99 |
| 2006/0117856 A1 | * | 6/2006 | Orr et al. | 73/700 |

FOREIGN PATENT DOCUMENTS

| | | |
|---|---|---|
| EP | 1 166 813 | 1/2002 |
| EP | 1 177 810 | 2/2002 |
| WO | WO 92/11054 | 7/1992 |
| WO | WO 98/57691 | 12/1998 |
| WO | WO 02/26305 | 4/2002 |
| WO | WO 02/053217 | 7/2002 |

* cited by examiner

AIR ASSISTANCE APPARATUS FOR COMPUTING THE AIRFLOW PROVIDED BY ONLY MEANS OF PRESSURE SENSORS

This application is a U.S. National Stage of International application PCT/IB03/01403, filed Mar. 10, 2003 and claims benefit of U.S. provisional application Ser. No. 60/362,441, filed Mar. 8, 2002.

TECHNICAL FIELD

This invention concerns the field of apparatus to assist a patient respiration and more specifically an apparatus able to calibrate the tubes connected to the patient's mask and to the blower and to determine the airflow of the patient's from pressure measurement and from the tube calibration.

BACKGROUND ART

In many treatments apparatus are used to provide patients with air. More frequently it is used for patients with a breathing deficiency caused for example by the weakness of the breathing system or by obstructive apneas during the sleep. In those cases it is important to control the pressure of the air delivered to the patient. With respiratory insufficient patients, apparatus providing air at a higher pressure help to compensate the weakness of the patients lungs. In the case of patients suffering of sleep apneas, providing the air at a higher pressure removes the obstruction of the upper airways.

In order to provide a correct treatment, it is required to accurately know the value of airflow the patient is provided with. Usually the apparatus determine the airflow by measuring airflow in the patient circuit (between the blower and the mask) using an airflow sensor. Airflow sensors can be based on high sensitivity differential pressure sensors measuring the pressure drop across a low resistance or using pitot tubes, or hot wire airflow sensors. Another commonly used mean to evaluate the airflow is by measuring the blower parameters such as speed, current consumption and power.

SUMMARY OF THE INVENTION

The first object of the invention is to determine the airflow at the patient's mask, without using sensors like airflow sensors that are expensive or motor consumption or rotation sensors that are not accurate especially at low flows.

The invention thus concerns to assist a patient respiration by delivering air to a patient through a mask, said mask being designed to be connected on one first extremity of a tube, said apparatus comprising:
- a control unit to adjust the pressure delivered by the blower of said apparatus,
- a first pressure sensor for sensing the pressure PM at the first tube extremity and being connected to the control unit, and
- a second pressure sensor for sensing the pressure PB at the air output of said blower and being connected to said control unit.

These elements are comprised in the apparatus in order that, when a tube is connected to the mask and connected to said apparatus on its second extremity, the air flowing from the apparatus to the mask, said control unit is able to calculate the airflow at said second extremity of the tube from the pressures PM and PB and from the airflow resistance coefficient $K_T$ of the tube An other implementation of the apparatus according to the invention is to provide an apparatus being able to calculate the coefficient $K_T$ by using a shell with a traversing hole having a known airflow resistance coefficient $K_s$. This enables to use tubes of different sizes, and even tubes with different standards of airflow resistance coefficients.

A further implementation of the apparatus according to the invention is that the pressure control unit comprises an estimation module connected to the means for detecting the patient's breathing parameters, in order that the estimation module is able to determine when the patient is inspiring or expiring and in response the pressure to apply to the patient's mask, so that the control unit adjusts the pressure delivered by the blower.

Further implementations enable modulating the pressure of the provided air in response to the patient's breathing parameters and events which occur in the patient's breathing.

BRIEF DESCRIPTION OF FIGURES

The purposes, objects and characteristics of the invention will become more apparent from the following description when taken in conjunction with the accompanying drawings in which.

DETAILED DESCRIPTION OF THE INVENTION

Figure 1:
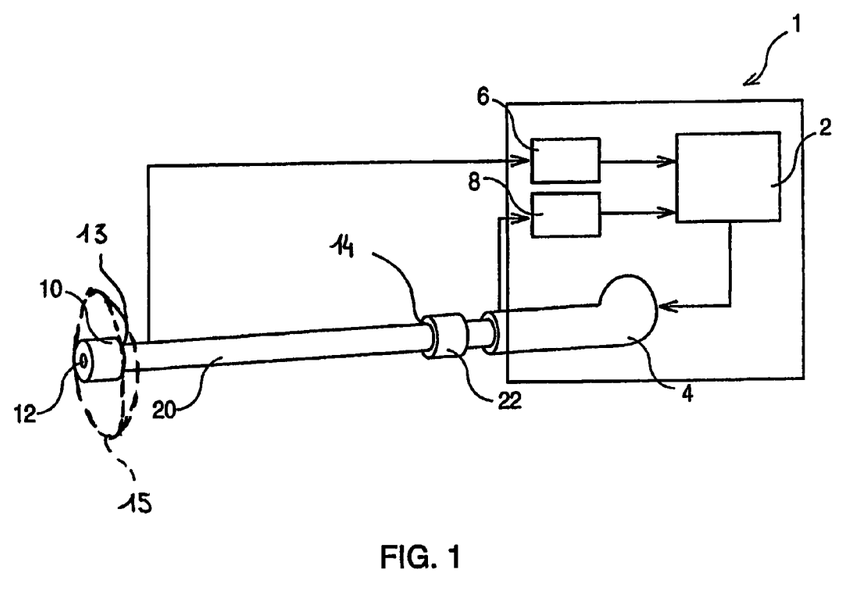
FIG. 1 represents the apparatus according to the present invention when used according to a preferential implementation.

Ordinary tubes used in an air assisting apparatus usually comprise a pressure sensing tube to measure the pressure at the end of the tube. The apparatus according to the present invention is based on this characteristic. As represented on FIG. 1, the apparatus 1 is connected to the tube 20 by the air inlet and connected to the pressure sensing tube of the tube. The pressure sensing tube is connected to a first pressure sensor 6 comprised in the apparatus. If no sensing tube is comprised, a mean will be connected at a first pressure sensor of the apparatus. Because the tube 20 diameter value is much smaller than the tube 20 length value, the pressure drop in the tube is defined by the following equation:

$$\Delta p = K_T \text{airflow}^2$$

wherein:

$K_T$ represents a constant coefficient characteristic of the tube, $\Delta p$ represents the difference of pressure between the two tube extremities, and airflow is the volume of air per time crossing the tube.

The apparatus has sensors that measure the pressure PB at the apparatus air outlet. As the apparatus is sensing pressure on both sides of the tube, knowing the tube coefficient k is allowing the system to compute the airflow by measuring the pressure drop. The present implementation consists in operating in a mode where precise airflow is required. A shell 10 which is a cap which comprises a small hole 12 at his top is placed to close one extremity of the tube, the other extremity of the tube being connected to the air outlet of the blower 4 of the apparatus 1. This calibration shell 10 has an airflow resistance coefficient $K_S$ which is a characteristic of it.

Considering that PB being the pressure sensed at the output of the apparatus and PM being the pressure sensed at the calibrated termination, S0 being known, we have $$\text{Airflow} = K_S \cdot \sqrt{PM}$$

$$\text{as } \Delta p = K_T \cdot \text{airflow}^2 \text{ then } K_T = \frac{(PB - PM)}{(K_S^2 \cdot PM)}$$

The apparatus is thus able to determinate the tube coefficient $K_T$.

The calibration process takes advantages of having a number of measurements made at different pressures levels and by averaging them can get a more accurate $K_T$ value.

Example of a 1.8 m tubing Ø15 mm:

The calibration termination has a S0 coefficient of 18 (airflow units are in LPM)

PB is measured at 9.90 hPa

PM is measured at 7.72 hPa

This is giving k=0.000871

Meaning then that the airflow is: 50.02 LPM

Figure 2:
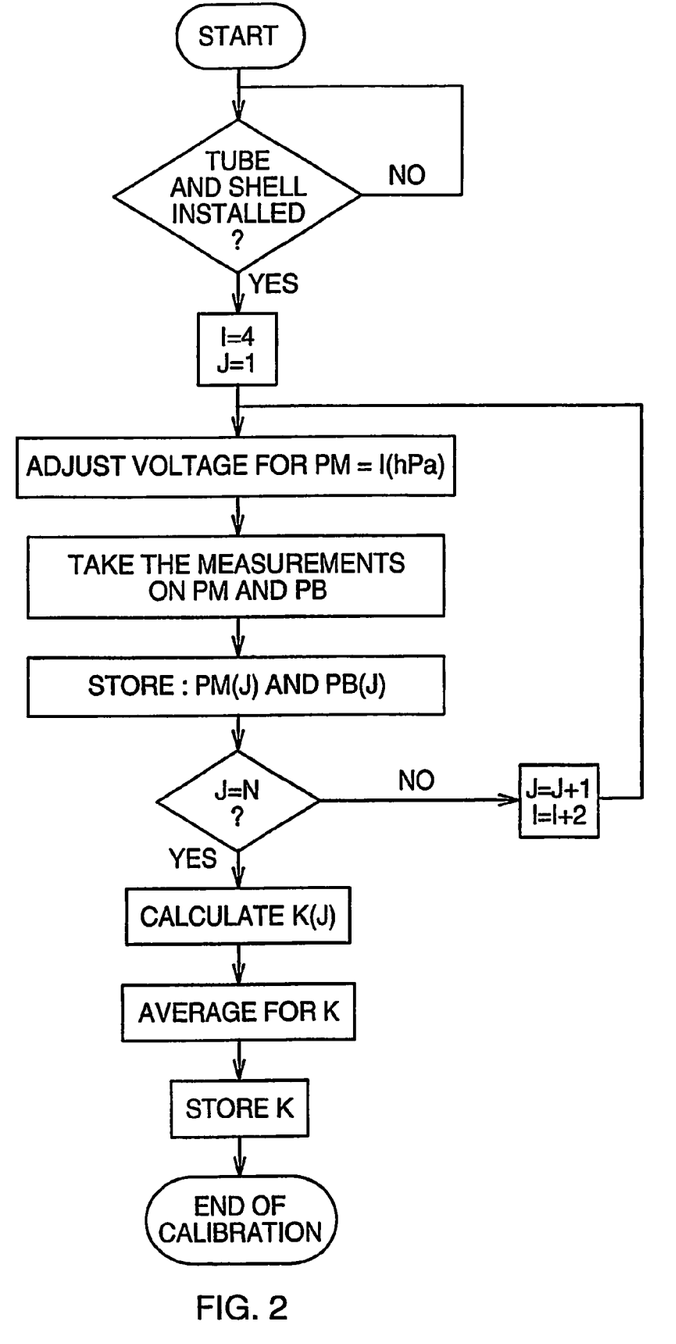
FIG. 2 represents the flowchart of the calibration of a tube by the apparatus.

When using a new tube, the calibration process is entered, notably at the request of a clinician or a qualified user. The apparatus is expecting the calibrating shell to be hooked as described in FIG. 1. The flowchart represented in FIG. 2 is showing an example of a series of measurements resulting in the $K_T$ coefficient calculation, then the tube coefficient $K_T$ is recorded and all the upcoming sessions will be based on this new tube coefficient. When the tube 20 and the calibrating shell 10 are installed, the value J corresponding to the number of one measure is set equal to 1 and associated to a number I corresponding to the value of the pressure provided by the blower 4, this I number being for example equal to 4 hPa when the calibration starts. Then the Pulse Width Modulation (PWM) 31 voltage is applied in order to deliver the pressure PM sensed at the calibrated termination which is the calibrating shell 10. The pressure PM and the pressure PB are measured and associated to the J number corresponding to the measure. If J does not equal the number of measures N required to calculate the $K_T$ average, the next measure is taken which means that J is incremented by 1. The next measure is preferentially made for a pressure incremented of 2 hPa, which means that I is incremented by two. When the number of measures required N is reached, the data associated to each measure are computed and enable to associate a tube coefficient $K_T$ value to each corresponding measure J. This enables calculating of an average of the $K_T$ value. For example if eight measures are required, J and I will be incremented 7 times before calculating the tube coefficient k value. This also enables rejecting the tube if its standard does not correspond to the kind of tube which can be used with the apparatus 1. The $K_T$ value will then be used for the airflow computation. When at least one filter 22 is placed at a first extremity 13 of tube, the control unit 2 is able to calculate the airflow at the second extremity 14 of the tube from the measured pressures PM and PB and from the airflow resistance coefficient $K_T$ of said tube and from the airflow resistance coefficient KF of said filter.

The apparatus as described above, wherein the control unit comprises offset compensation means for compensating the possible difference of gauging between the two pressures.

Another embodiment of the present invention is improving the sensitivity of the airflow measurement at low values, by gauging the pressure sensors.

Low flows accuracy is important in an air delivery apparatus especially when triggering between inspiration and expiration where sensitivities as low as 5 l/mn are required.

A classical 22 mm diameter breathing tube will present a pressure drop (PB−PM) of 0.01 hPa with an airflow of 5 l/mn, so it is mandatory to consider a signal amplification after the subtraction.

But this amplification cannot be done without a prior offset compensation. The apparatus according to the preferential implementation enables to correct this difference of gauging.

As previously described, using two pressure sensors at both ends of a breathing circuit tube, can give an accurate value of airflow, but due to physical constraints, for low flows accuracy, there is a need for amplification.

Due to the manufacturing process of airflow sensors, most of them are presenting a Voltage vs. Pressure relationship like:

$$Vout = Voffset + Kps \cdot Pr$$

With

Vout being the output voltage

Voffset being the constant that can change drastically from one sensor to another within the same lot and that drifts slowly due to aging.

Kps: the gain in volts/hPa of the pressure sensor that is usually stable.

Pr: the difference between pressure sensors 6 and 8

Given the previous equation, subtracting the two voltages of the two pressure sensors will then give:

$$VPbPm = VoffPm - VoffPb + Kps*(Pb - Pm)$$

With

VPbPm is the Voltage result of the subtraction

VoffPm is the offset of the Pm pressure sensor

VoffPb is the offset of the PB pressure sensor

Kps is the gain in volts/hPa of the pressure sensors

By offset it is meant that the constant which corresponds to the difference between the pressure measured by one sensor and the absolute value of pressure.

Figure 3:
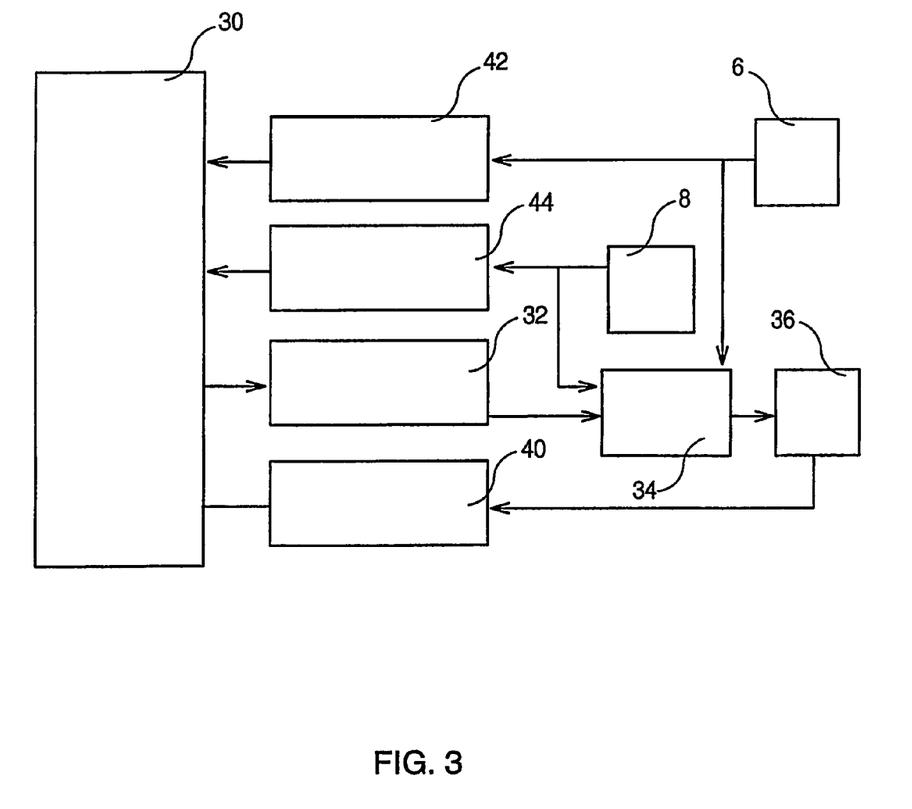
FIG. 3 represents a device of the apparatus according to present invention.

The invention takes advantages of a well known state of the apparatus when no patient is connected to the apparatus, and no pressure is generated by the blower. During this state The PM and PB values have the same value as the ambient pressure. The control unit 2 comprises offset compensation means for compensating the possible difference of gauging between the two pressure sensors 6 and 8.

Figure 4:
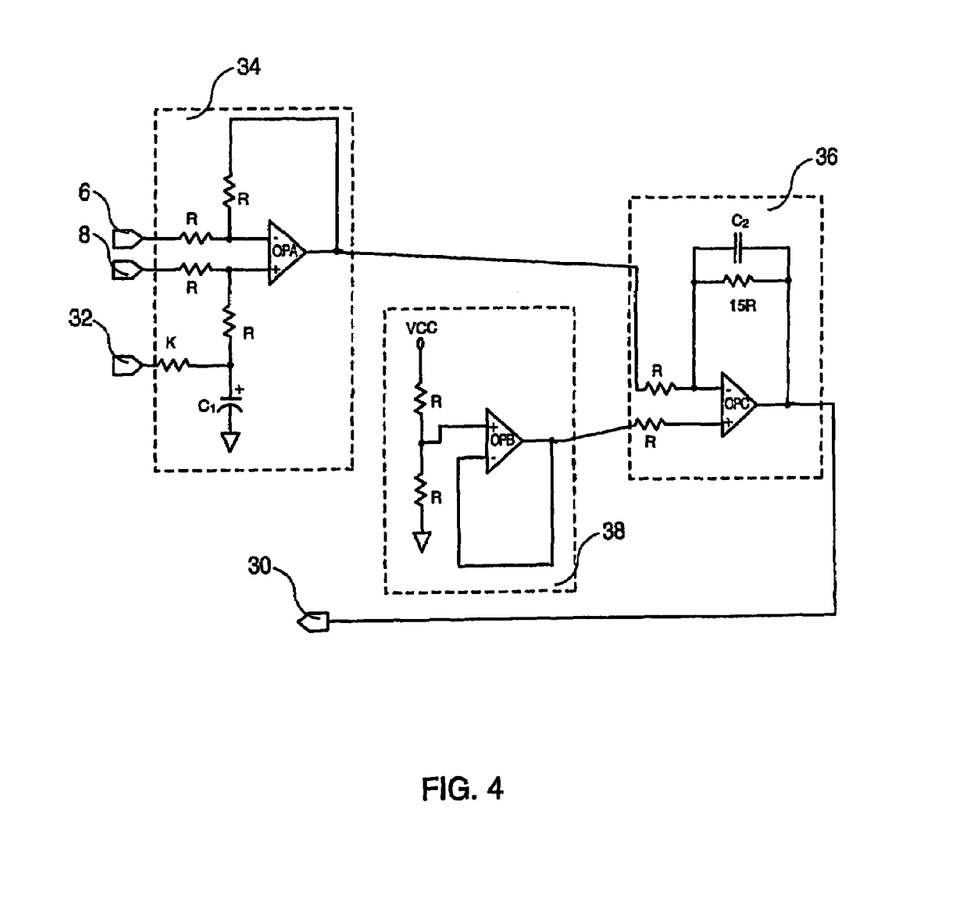
FIG. 4 represents the electric schema of the device represented in FIG. 3.

Preferentially the offset compensation means comprise:
- a digital to analog converter 32 connected to a microprocessor 30 in order to convert microprocessor's digital data in analog data,
- an analog substractor 34 having inputs connected to the second pressure sensor, to the first pressure sensor, and to said digital to analog converter;

said microprocessor calculating, when the blower is not functioning, the difference between the two pressures measured by said first and second pressure sensors and then sending the value C of this difference to said digital to analog converter, which converts said value C in analog data and drive it to said analog subtractor, which subtract the pressure $P_B$ measured by said second pressure sensor and said value C to the pressure $P_M$ measured by said second pressure sensor and send the corresponding result D to the microprocessor, which will modify the C value until said D result equals zero, said microprocessor capturing the C value when said D result equals zero, enabling the microprocessor which uses the pressure sensors to control the apparatus to correct the difference of offsets between the pressure sensors.

Preferentially the apparatus comprises an analog amplifier 36 connected to said analog subtractors 34 and 38 in order to amplify the signal corresponding to said D result and to send it to the microprocessor 30, thus enabling the microprocessor to have an accurate adjustment of said value C until the result D reaches the value zero.

The apparatus can also comprise analog to digital converters 42, 44 and 40 connected between the microprocessor 30 and the said first pressure sensor, between the microprocessor and the said second pressure sensor, and between the microprocessor and the said analog amplifier, so that the microprocessor is provided with only digital data.

With a non standard calibration tube, the process for calibrating a tube used in the apparatus to assist patient's respiration, comprises:
- connecting a first extremity 13 of said tube 20 to the blower of an apparatus,
  - if the tube is not provided with a pressure sensor at its second extremity, placing said second pressure sensor at said second extremity,
  - connecting said second extremity to a shell 10 with a traversing hole 12 having a known airflow resistance coefficient $K_s$,
- switching the blower on, and instructing said control unit 2 to measure the pressures on both said first and second pressure sensors,
  - calculating the value of the tube airflow resistance coefficient $K_t$ from these measured pressures and from the said coefficient $K_s$.

Figure 8:
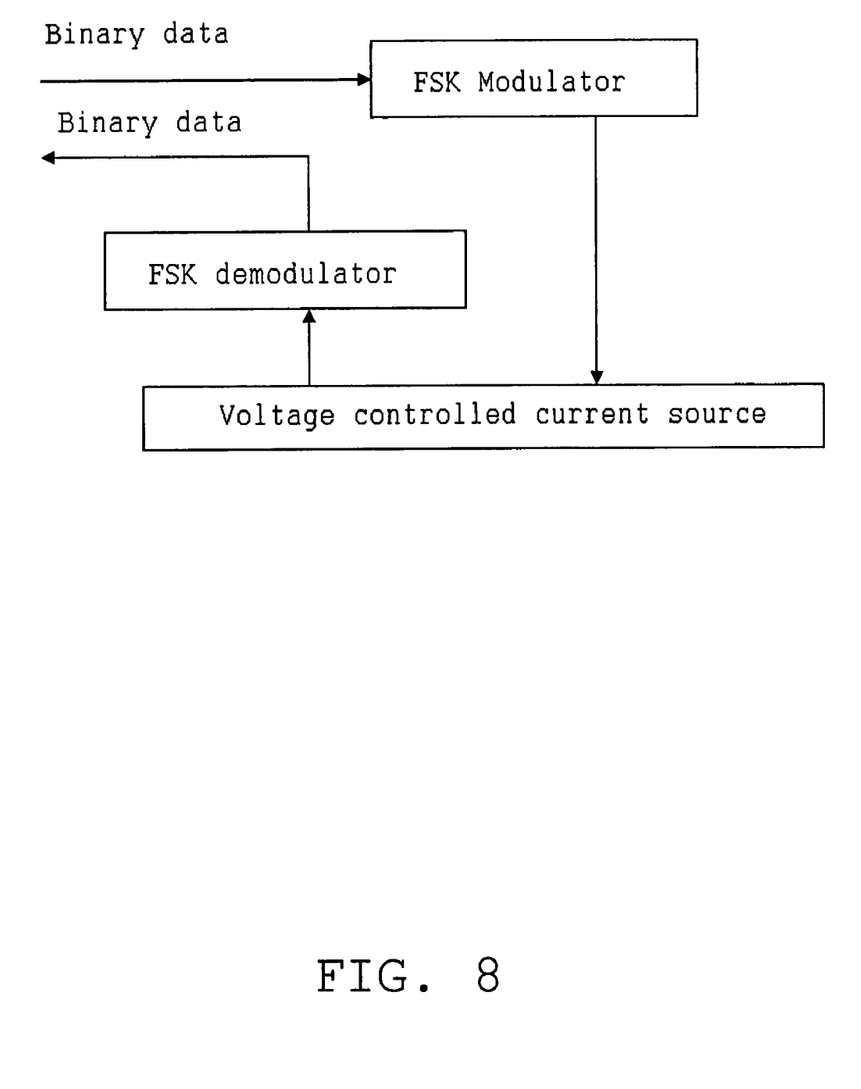
FIG. 8 represents the relationship between Frequency Shift Keying (FSK) modulator and the voltage controlled current source.

The apparatus can also comprise a Frequency Shift Keying (FSK) modulator which transforms the binary data sent by the apparatus sensors or elements in a modulation of the frequency of the tension applied on a voltage controlled current source, connected to the external power supply, so that the voltage controlled current source transmit the modulation corresponding to the data, a FSK demodulator converting the voltage frequency modulation into binary data and transmit to the elements, so that each sensor or module connected to the power source is able to receive or transmit information.

The apparatus can also be used in a set for calibrating a tube used in apparatus to assist patient's respiration comprising the apparatus according to present invention and a calibrating shell 10 with a traversing hole 12 having a known airflow resistance coefficient $K_s$.

Figure 5:
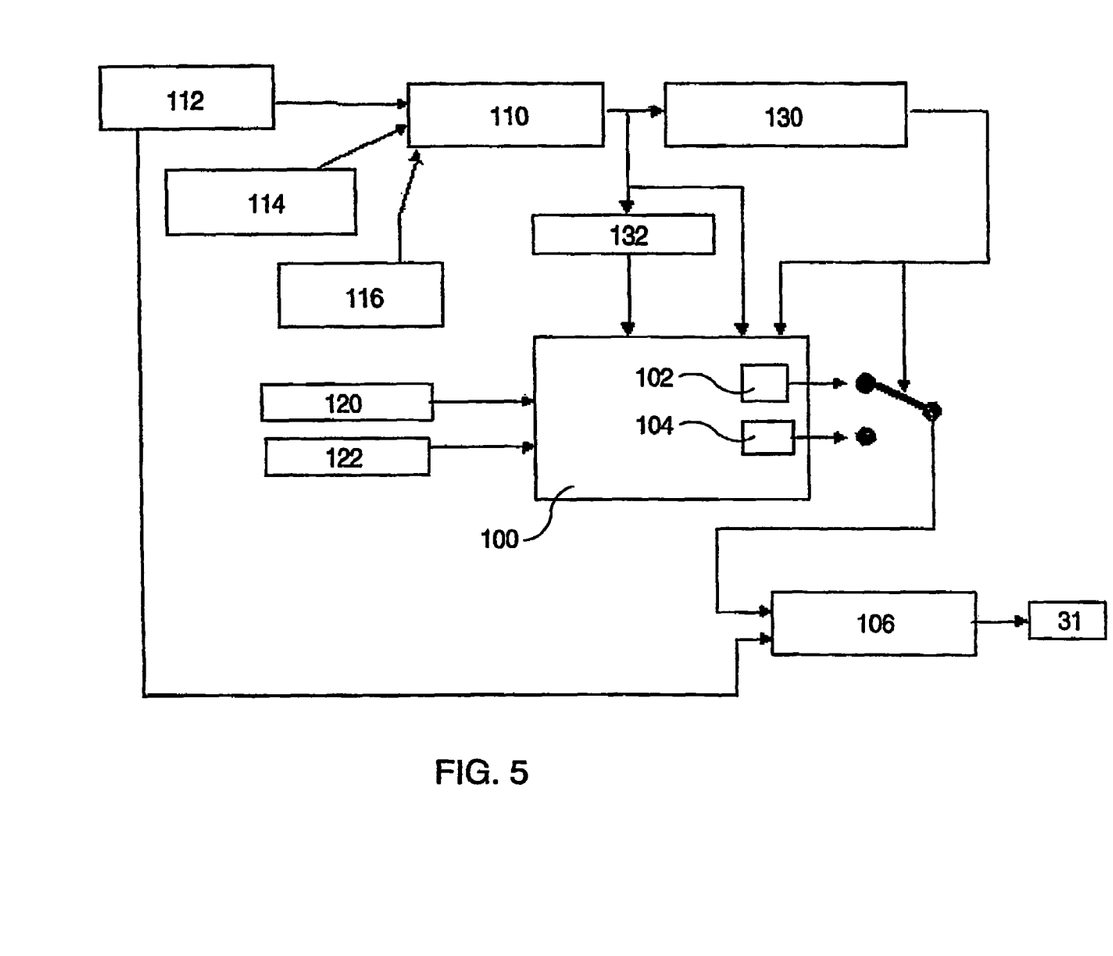
FIG. 5 represents an implementation of the apparatus.
Figure 6:
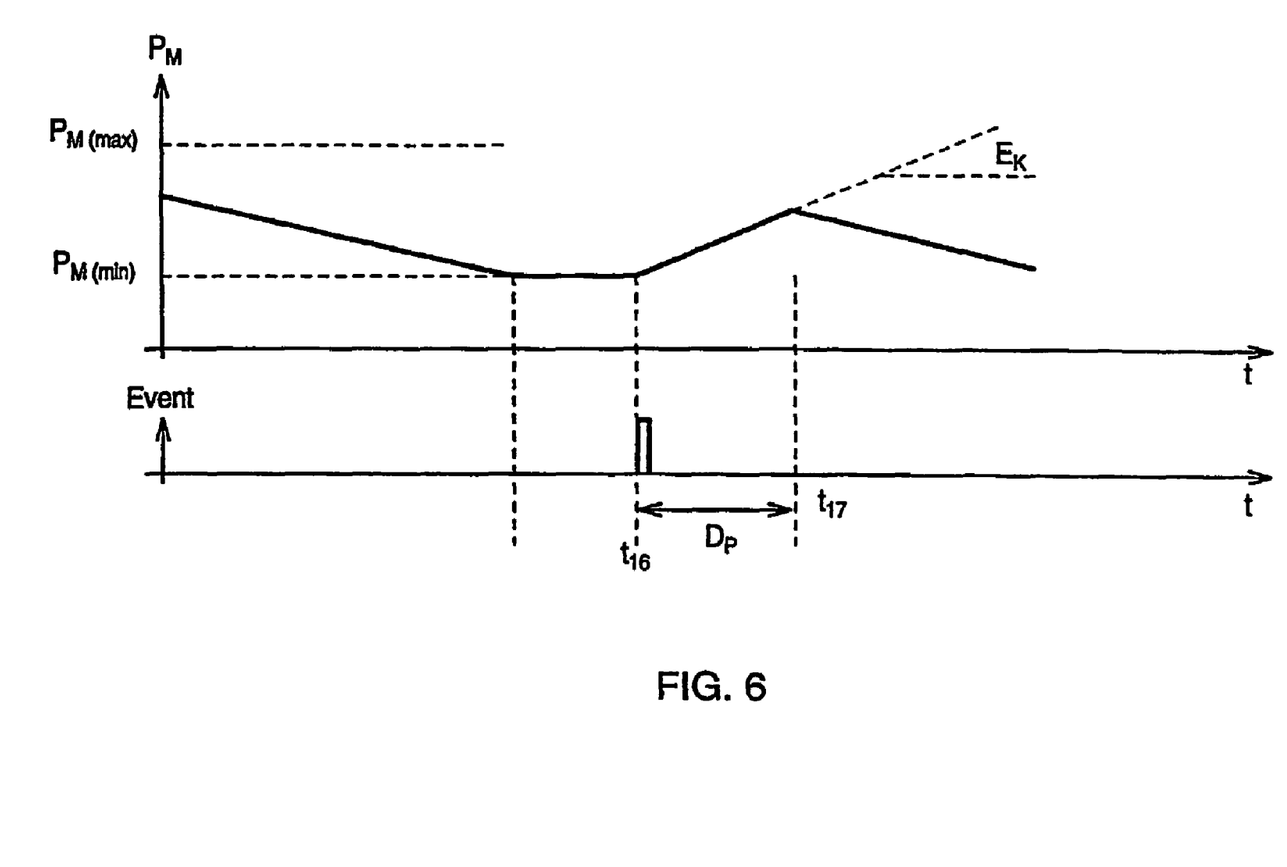
FIG. 6 represents the way the apparatus reacts to events occurring in patient's breathing.
Figure 6B:
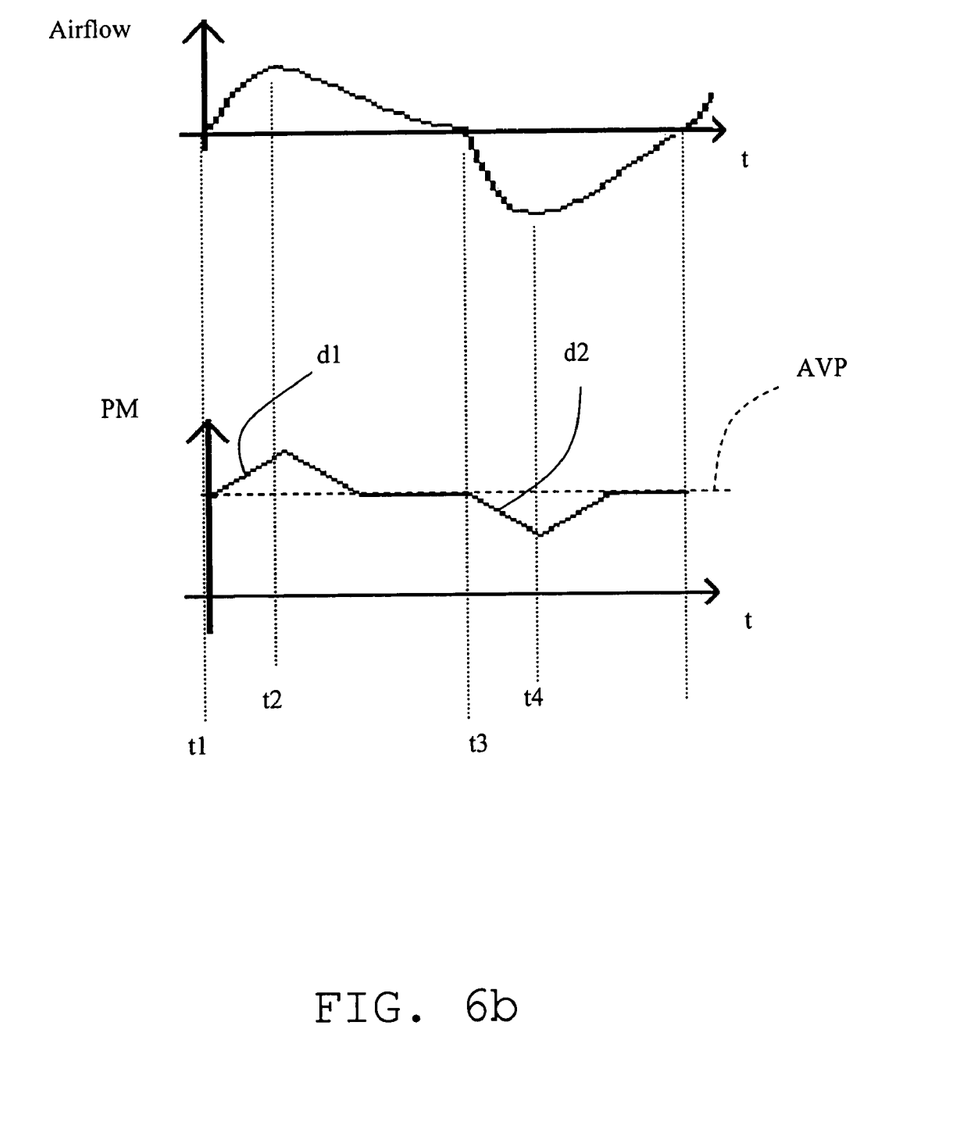
FIG. 6(b) represents the auto-adjustment of Example 2.

The apparatus enables modulation of the pressure to the patient in respect to the illness to treat. Due to the airflow computation, the apparatus has the capacity to differentiate the two basic states of the respiration: inspiration and expiration. The control unit comprises a nonvolatile memory 120 in which the control unit stores, as two values, the pressures measured at each pressure sensor. The sensors provided in the apparatus enables the pressure control unit to control the pressure of the air delivered. The outputs of the Estimator are the value of the inspiration pressure PI which is the pressure maintained at the patient's mask 15 during the inspiration, and the value of the expiration pressure PE which is the pressure maintained at the patient's mask 15 during the expiration. The data of the pressures PM 112 and PB 114 which are sensed at the extremities of the tube and the data 116 of the tube coefficient $K_T$ enable the airflow computation. This computation 130 enables the computation of the inspiration and expiration, this latest computation enables the estimation module 100 to determinate, which step of the patient's breathing is occurring. A breath estimation step is qualifying a breath in shape, energy (volume) and frequency. The clinician or a qualified user enters parameters of the delivered pressures for the expiration phase and the inspiration phase. The clinician also enters parameters defining how the estimation module 100 is going to react following events detected in the breath estimator 132. It is well known that a feedback of the patient with his treatment is helping compliance, thus the patient can have an access to a parameter ranging from min to max that is qualified to be "comfort vs. efficiency". This patient setting is having the weight that the clinician is giving to it, from pure placebo effect to some level of effects. Basically the patient settings 122 are applied in the normal breath situation or/and have a limited action on the pressure regulation. It is also possible that the airflow is an input to the estimation module 100. Thus, with the data inputs concerning the breath estimation (and clinical symptoms or event associated with), the inspiration/expiration computation and the clinical settings, and possibly the airflow computation and patient settings, the control unit 2 by the estimation module 100 is able to determinate the pressures required PI and PE. Those two values can be addressed to two different outputs 102 and 104 where a switch is able, relative to the inspiration/expiration computation, to connect to the required output regarding if the patient is breathing in or out. The control unit 2 comprises a pressure control loop 106 which, by comparing the pressure measured in the mask 15 and the value of pressure required PI or PE, is able to adjust the Pulse Width Modulation tension PWM in order to obtain the correct pressure in the mask 15. The FIG. 6 represents one pattern of the pressure of treatment provided according to the airflow due to the patient breathing. In this example, the clinical technician has set a special modulation of pressures Pi and Pe during respectively the inspiration and the expiration; after a while as no special event occurs the values of the two pressures are changed.

Figure 7:
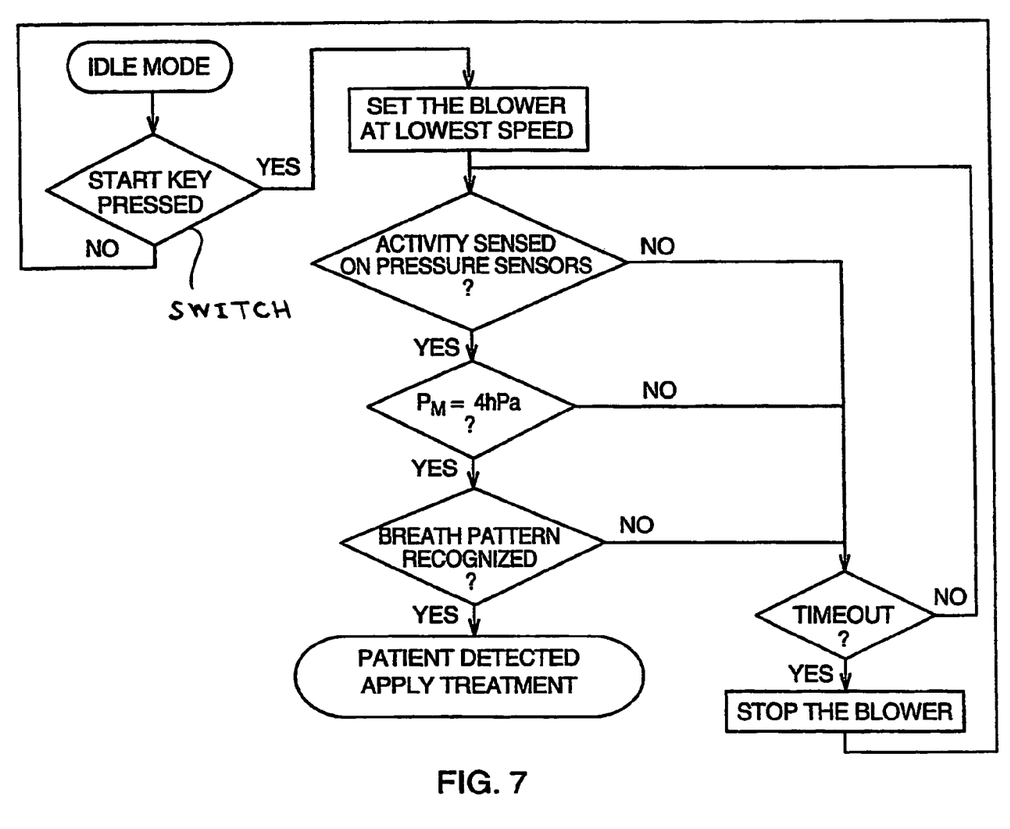
FIG. 7 represents how the apparatus operates to detect the presence of a patient at the mask.

The apparatus has a two steps strong recognition process in order to prevent false start of the apparatus when the mask 15 is not on the patient's face and to prevent starting a new treatment session. When the apparatus is started by the patient by using the keyboard, for example and as represented in FIG. 7 by using the start key, the blower 33 is kept turning at a very low speed, waiting for some activity on the mask pressure sensors 6. When an activity is detected, the apparatus is instantaneously trying to bring the pressure at the apparatus outlet at a minimum starting pressure SP of 4 hPa. When this pressure is reached the apparatus tries to identify at least one breath to start the process according to the settings. When the mask 15 is not applied against something, like a hand or the patient's face, no activity is detected. Then if a maximum time since the apparatus start has been spent (the timeout is reached), the blower is stopped. On the contrary, the apparatus keeps on waiting for an activity on the pressure sensors. When the mask 15 is not applied correctly the pressure can not reach 4 hPa. Then if the timeout is reached the blower is stopped, on the contrary the apparatus waits to detect some activity on the pressure sensors. When the mask 15 is not applied on the patient's face no breath pattern is recognized. Then the blower is stopped if the timeout is reached. On the contrary the apparatus waits to detect some activity on the pressure sensors. The timeout checking prevents the blower keeping turning on if the patient does not start the treatment and forgets to start the blower. A further advantage of this implementation is that if a patient is connected, bringing the pressure instantaneously to 4 hPa will prevent $CO_2$ rebreathing.

The following examples demonstrates the way the estimation module 100 modulates the pressure value $P_M$ to apply to the patient's mask.

EXAMPLE 1

Variations of the Pressure of the Average Pressure of Treatment as a Function Time According to Detected Events In a preferential embodiment the average pressure of treatment on one breathing step is not constant in time and will be modulated by the estimation module 100 according to the events occurring, such as snoring or apneas.

The apparatus will try to reduce the average pressure of treatment value, thus enhancing the patient comfort while breathing against the apparatus. The clinician set a minimum average pressure of treatment Ptmin and a coefficient $N_{OEK}$ expressed in hPa/s.

As represented on FIG. 6 when no events are detected the average pressure of treatment value will follow the equation:

$$PT(t)=MAX(PT(t-\epsilon)-(NOEK\times\epsilon), PT\min)$$

$\epsilon$ being the sampling time, the MAX function is returning the greatest value of its two members. The average pressure value AVP, corresponding to the pressure of treatment PT on one breath thus decrease linearly until it reaches the minimum set by the clinician and stays constant until an event occurs. The average pressure is changed each sampling time which correspond to one single breath (one inspiration and one consecutive expiration).

If an event is detected, a 3 steps process is initiated:
Step 1: the estimation module, looking in the clinical settings is defining if the event has to affect the average value of pressure PT.
Step 2: If so the estimation module looking in clinical settings, will define a persistence delay $D_p$. In the example of FIG. 6, a snore is detected at $t_{16}$, the persistence delay DP $=t_{17}-t_{16}$ could be set to 2 minutes.
Step 3: A Ek parameter in hPa/s is extracted from clinical settings and balanced with an eventual ongoing event. The estimation module will determine the Ek corresponding to the event which occurs or has occurred and linearly increase the average pressure of treatment with Ek as slope coefficient. AVP will then follow the equation:

$$PT(t)=MIN(PT(t-\epsilon)+(EK\times\epsilon), AVP\max)$$

$\epsilon$ being the sampling time, the MIN function is returning the smallest value of its two members.

During the persistence delay even if no event occurs the estimation module will keep on increasing the average pressure of treatment PT.

EXAMPLE 2 d1, d2 Auto Adjustment

On the FIG. 6 d1 and d2 have two different behaviors, according to t2 and t4 definitions. t2 is defined when the absolute value of airflow starts to decrease within the inspiration phase or shows a fixed delay after t1. t4 is defined when the absolute value of airflow starts to decrease within the expiration phase or shows a fixed delay after t3.

If t2 and t4 are defined according to the airflow waveform then no auto-adjustment is occurring. If not, following the same rules than AVP, the d1 and d2 can also be affected by the events. In the case when d1 & d2 are not locked by the breath waveform following the same process, d1 & d2 can also be adjusted according to events in the case.

The invention claimed is:

1. An apparatus to assist a patient's respiration by delivering air to said patient through a mask, said mask being designed to be connected on a first extremity of a tube, said apparatus comprising:
a control unit to adjust the pressure delivered by a blower of said apparatus,
a first pressure sensor for measuring a first pressure, said first pressure sensor being connected to said control unit, and
a second pressure sensor for measuring a second pressure at an air output of said blower, said second pressure sensor being connected to said control unit;
wherein when a tube is connected between said apparatus and a calibrating shell with a traversing hole having a known airflow resistance coefficient $K_S$, the air flows from the apparatus to said calibrating shell, and the measured pressures are sent to said control unit, which calculates a tube airflow resistance coefficient $K_T$ based on said first and second measured pressures and said known airflow resistance coefficient $K_S$,
wherein when a tube is connected to said mask and connected to said apparatus on a second extremity of said tube, the air flows from the apparatus to the mask, and said control unit calculates the airflow at said second extremity of the tube based on said first and second pressures and said airflow resistance coefficient $K_T$ of said tube.

2. The apparatus according to claim 1, wherein the control unit comprises an offset compensation means for compensating a possible difference of gauging between the two pressure sensors.

3. The apparatus of claim 1, wherein said first and second pressure sensors sense the pressure at both extremities of said tube.

4. An apparatus to assist a patient's respiration by delivering air to said patient through a mask, said mask being designed to be connected on a first extremity of a tube, said apparatus comprising:
a control unit to adjust the pressure delivered by a blower of said apparatus,
a first pressure sensor for measuring a first pressure, said first pressure sensor being connected to said control unit, and
a second pressure sensor for measuring a second pressure at the air output of said blower, said second pressure sensor being connected to said control unit;
wherein when said tube is connected to said mask and connected to said apparatus on a second extremity of said tube, the air flows from the apparatus to the mask, and said control unit calculates the airflow at said second extremity of the tube based on said first and second pressures and an airflow resistance coefficient $K_T$ of said tube; and
wherein the control unit comprises an offset compensation means for compensating the possible difference of gauging between the two pressure sensors.

5. The apparatus according to claim 4, wherein when said tube is connected between said apparatus and a calibrating shell with a traversing hole having a known airflow resistance coefficient $K_S$, the air flows from the apparatus to said calibrating shell, the measured first and second pressures are sent to said control unit, which calculates the tube airflow resistance coefficient $K_T$ based on said measured first and second pressures and said known airflow resistance coefficient $K_S$.

6. The apparatus according to claim 4, wherein said offset compensation means comprises:
- a microprocessor,
- a digital to analog converter connected to said microprocessor in order to convert said microprocessor's digital data to analog data,
- an analog subtractor having inputs connected to the second pressure sensor, said first pressure sensor, and said digital analog converter,
- wherein when the blower is not functioning, said microprocessor calculates the difference between the first and second pressures measured by said first and second pressure sensors to obtain a value C, and then sends the value C of said difference to said digital to analog converter, which converts said value C to analog data and drives said value C to said analog subtractor,
- wherein said subtractor subtracts the second pressure measured by said second pressure sensor and said value C from the first pressure measured by said first pressure sensor and sends the corresponding result D to the microprocessor,
- wherein said microprocessor modifies the C value until said result D equals zero, said microprocessor capturing the C value when said result D equals zero, enabling the control unit to correct the difference of offsets between the pressure sensors.

7. The apparatus according to claim 6, further comprising an analog amplifier connected to said analog subtractor in order to amplify the signal corresponding to said result D and to send said result D to said microprocessor, thus enabling said microprocessor to have an accurate adjustment of said value C until said result D reaches the value zero.

8. The apparatus according to claim 7, further comprising analog to digital converters connected between the microprocessor and said first pressure sensor, between the microprocessor and said second pressure sensor, and between the microprocessor and said analog amplifier, so that the microprocessor is provided with only digital data.

9. The apparatus according to claim 4, wherein when at least one filter is placed at said first or second extremity of said tube, said control unit calculates the airflow at said second extremity of the tube based on said measured first and second pressures, the airflow resistance coefficient $K_T$ of said tube, and an airflow resistance coefficient $K_F$ of said filter.

10. The apparatus according to claim 4, wherein said control unit comprises a nonvolatile memory in which the control unit stores two values corresponding to said first and second pressures measured at each of said first and second pressure sensors, when said control unit forces the blower to deliver a determined constant pressure I at one of the two sensors, so that when at least two values corresponding to two different said determined constant pressures I are stored, the control unit calculates an average of said airflow resistance coefficient $K_T$.

11. The apparatus according to claim 4, wherein said control unit comprises an estimation module connected to a means for detecting the patient's breathing parameters, such that the estimation module determines when the patient is inspiring or expiring, and in response determines the pressure to apply to the patient's mask, so that the control unit adjusts the pressure delivered by the blower.

12. The apparatus according to claim 11, wherein the control unit comprises a nonvolatile memory in which a clinician can enter clinical settings comprising at least the treatment pressure and possibly the pressure to apply according to the patient's breathing parameters, said estimation module applying the pressure according to these clinical settings and to the patient's breathing parameters.

13. The apparatus according to claim 12, wherein the patient can enter patient settings in said nonvolatile memory, said estimation module applying the pressure according to said patient settings and to the patient's breathing parameters within bounds given by the clinician settings.

14. The apparatus of claim 11, in which the estimation module is able to determine that an event ($E_1$, $E_2$ or $E_3$) occurs in said patient's breathing, thus enabling said control unit to adjust the tension to apply to the blower to adjust the pressure at said patient's mask.

15. The apparatus of claim 11, wherein said means for detecting the patient's breathing parameters enable the control unit to compute the airflow at said patient's mask, said estimation module determining that an event ($E_1$, $E_2$ or $E_3$) is occurring with the airflow parameters or shape.

16. The apparatus according to claim 11, wherein said estimation module has an inspiration output where said estimation module sets the first pressure value during inspiration and wherein said estimation module has an expiration output, and wherein said estimation module sets the first pressure value during expiration, said control unit comprising a switch which is connected alternatively to the inspiration output or expiration output according to the patient's breathing.

17. The apparatus according to claim 11, wherein the apparatus further comprises a starting means which when actuated enables the estimation module to determine if a breathing activity is detected, the estimation module sending an instruction to stop the blower if no activity is sensed after a given delay.

18. The apparatus of claim 4, further comprising:
- a Frequency Shift Keying (FSK) modulator which transforms the binary data sent by the apparatus sensors or elements in a modulation of the frequency of the tension applied on a voltage controlled current source, connected to an external power supply, so that the voltage controlled current source transmits the modulation corresponding to the data, and
- a FSK demodulator which converts the voltage frequency modulation into binary data and transmits it to the elements, so that each sensor or module connected to the power source is able to receive or transmit information.

19. A kit for calibrating a tube used in apparatus to assist said patient's respiration comprising:
- the apparatus according to claim 4, and
- a calibrating shell with a traversing hole having a known airflow resistance coefficient $K_S$.

20. A process for calibrating said tube used in said apparatus to assist a patient's respiration by using the apparatus according to claim 4, said process comprising the steps of:
- connecting said second extremity of said tube to the blower of said apparatus,
- connecting said first extremity to a calibrating shell with a traversing hole having a known airflow resistance coefficient $K_S$,
- connecting said first pressure sensor to measure the first pressure at said first extremity of said tube,
- switching the blower on,
- instructing said control unit to measure the first and second pressures at said first pressure sensor and said second pressure sensor, said second pressure being measured at an outlet of said blower, and calculating the value of the tube airflow resistance coefficient $K_T$ based on said measured first and second pressures and said known airflow resistance coefficient $K_S$.

21. A process for calibrating the tube used in apparatus to assist said patient's respiration, and for calibrating the tube by using the apparatus according to claim 4, said process comprising the steps of:
(1) connecting said second extremity of said tube to the blower of said apparatus,
(2) connecting said first extremity of said tube to a calibrating shell with a traversing hole having a known airflow resistance coefficient $K_S$,
(3) connecting said first pressure sensor to measure the first pressure at said first extremity of said tube,
(4) switching the blower on,
(5) fixing at a value I the pressure provided and measured on one of said two pressure sensors,
(6) instructing said control unit to measure the pressures at said first pressure sensor and second pressure sensor, said second pressure being measured at an outlet of said blower,
(7) storing said first and second pressures as a measured pressure values associated with said value I,
(8) repeating steps 5 and 6 a number of times N, said value I being different for each time, so that each of said measured pressure values are associated with one value I, and
(9) calculating on average of the airflow resistance coefficient $K_T$ based on said first and second measured pressures and said known airflow resistance coefficient $K_S$.

22. A process for assisting a patient's respiration by delivering air to the patient through a mask, comprising the steps of:
providing an apparatus comprising a control unit for adjusting the pressure delivered by a blower of said apparatus, a first pressure sensor and a second pressure sensor, said second pressure sensor being provided at an air outlet of said blower, said first and second pressure sensors being connected to said control unit;
providing a tube, a calibrating shell and said mask;
calibrating said tube by
connecting a first extremity of said tube to said calibrating shell with a traversing hole having a known airflow resistance coefficient $K_S$ and connecting a second extremity of said tube to the air outlet of said blower;
switching said blower on, the air flowing from said apparatus to said calibrating shell;
measuring a first pressure at said first pressure sensor and a second pressure at said second pressure sensor;
sending the first and second measured pressures to said control unit, wherein said control unit calculates a tube airflow resistance coefficient $K_T$ based on said first and second measured pressures and said known airflow resistance coefficient $K_S$;
connecting said first extremity of said tube to said mask and applying said mask on the patient's face;
switching the blower on, the air flowing from said apparatus to said mask; and
measuring a first pressure at said first pressure sensor and a second pressure at said second pressure sensor, wherein said control unit calculates the airflow at said second extremity of said tube based on the first and second pressures and the airflow resistance coefficient $K_T$ of said tube.

23. The process according to claim 22, further comprising the step of:
compensating a possible difference of gauging between said two pressure sensors using an offset compensation means, wherein said control unit further comprises said offset compensation means.

24. The process of claim 22, wherein the first and second pressure sensors are sensing the pressure on both extremities of the tube.

25. A process for assisting a patient's respiration by delivering air to said patient through a mask, comprising the steps of:
providing an apparatus comprising a control unit comprising an offset compensation means for adjusting the pressure delivered by a blower of said apparatus, and first and second pressure sensors connected to said control unit;
providing a tube and said mask;
connecting a first extremity of said tube to said mask, connecting a second extremity of said tube to said apparatus on a second extremity of said tube, and applying said mask to the patient's face;
switching said blower on, the air flowing from said apparatus to said mask, wherein said control unit calculates the airflow at said second extremity of the tube based on first and second pressures and an airflow resistance coefficient $K_T$ of said tube; and
compensating a possible difference of gauging between said two pressure sensors using said offset compensation means.

26. The process according to claim 25, further comprising the steps of:
calibrating said tube by connecting said first extremity of said tube to a calibrating shell with a traversing hole having a known airflow resistance coefficient $K_S$ and connecting said second extremity of said tube to said apparatus;
switching said blower on, the air flowing from said apparatus to said calibrating shell;
measuring the first pressure at said first pressure sensor and the second pressure at said second pressure sensor; and
sending the first and second measured pressures to said control unit, wherein the control unit calculates the tube airflow resistance coefficient $K_T$ based on said measured first and second pressures and said known airflow resistance coefficient $K_S$.

27. The process according to claim 25,
wherein said offset compensation mean further comprises a microprocessor, a digital to analog converter connected to said microprocessor in order to convert said microprocessor's digital data to analog data, and an analog subtractor having inputs connected to the second pressure sensor, said first pressure sensor, and said digital analog converter,
the process further comprising the steps of:
calculating, when said blower is not functioning, the difference between the first and second pressures measured by said first and second pressure sensors with said microprocessor to obtain a value C, and sending the value C of the difference to said digital to analog converter, which converts the value C to analog data and drives the value C to said analog subtractor,
subtracting the second pressure measured by said second pressure sensor and the value C from the first pressure measured by said first pressure sensor with said subtractor and sending the corresponding result D to said microprocessor, and modifying the C value until the result D equals zero with said microprocessor, said microprocessor capturing the C value when said result D equals zero, enabling said control unit to correct the difference of offsets between said first and second pressure sensors.

28. The process according to claim 27, further comprising the steps of:
amplifying the signal corresponding to the result D with an analog amplifier connected to said analog subtractor, and
sending the result D to said microprocessor, thus enabling said microprocessor to have an accurate adjustment of the value C until the result D reaches the value zero.

29. The process according to claim 28, wherein said analog to digital converters are connected between said microprocessor and said first pressure sensor, between said microprocessor and said second pressure sensor, and between said microprocessor and said analog amplifier, so that said microprocessor is provided with only digital data.

30. The process according to claim 25, further comprising the step of calculating the airflow at said second extremity of the tube based on said measured first and second pressures, the airflow resistance coefficient $K_T$ of said tube, and an airflow resistance coefficient $K_F$ of said filter with said control unit, wherein at least one filter is placed at the first or second extremity of said tube.

31. The process according to claim 25, further comprising the steps of:
storing two values corresponding to the first and second pressures measured at each of said first and second pressure sensors in a non-volatile memory in said control unit when said control unit forces said blower to deliver a determined constant pressure I at one of said sensors, and
calculating an average of said airflow resistance coefficient $K_T$ when at least two values corresponding to two different said determined constant pressures I are stored.

32. The process according to claim 25, further comprising the steps of:
determining when the patient is inspiring or expiring with an estimation module connected to a means for detecting the patient's breathing parameters,
determining the pressure to apply to the patient's mask, and in response, adjusting the pressure delivered by said blower.

33. The process according to claim 32, further comprising the steps of:
entering into a non-volatile memory in the control unit clinical settings comprising at least the treatment pressure and optionally the pressure to apply according to the patient's breathing parameters, said estimation module applying the pressure delivered according to these clinical settings and to the patient's breathing parameters.

34. The process according to claim 33, wherein the patient can enter patient settings in said nonvolatile memory, said estimation module applying the pressure according to said patient settings and to the patient's breathing parameters within bounds given by the clinician settings.

35. The process of claim 32, further comprising the steps of:
determining that an event (E1, E2 or E3) occurs in said patient's breathing with said estimation module, and
adjusting the tension to apply to said blower to adjust the pressure delivered to said patient's mask with said control unit.

36. The process of claim 32, further comprising the steps of:
computing the airflow with said control unit at said patient's mask based on airflow
parameters received from a means for detecting the patient's breathing parameters, and determining that an event (E1, E2 or E3) is occurring based on the airflow parameters with said estimation module.

37. The process according to claim 32, further comprising the step of
setting the first pressure value during inspiration and providing said estimation module with an expiration output with said estimation module, and
setting the first pressure value during expiration with said estimation module,
wherein said control unit further comprises a switch which is connected alternatively to the inspiration output or expiration output according to the patient's breathing.

38. The process according to claim 32, further comprising the steps of:
determining if a breathing activity is detected with a starting means when said starting means is actuated, and
sending an instruction to stop said blower from said estimation module to said blower if no activity is sensed after a given delay.

39. The process of claim 25, further comprising the steps of:
transforming the binary data sent by the apparatus sensors or elements with a Frequency Shift Keying (FSK) modulator into a modulation of the frequency of the tension applied on a voltage controlled current source, connected to an external power supply,
transmitting the modulation corresponding to the data from the voltage controlled current source,
converting the voltage frequency modulation with an FSK demodulator into binary data,
transmitting the voltage frequency modulation to the apparatus sensors or elements, such that each sensor or module connected to the power source receives or transmits information.

40. The process of claim 25, further comprising the steps of:
providing a kit comprising said apparatus, a calibrating tube and a calibrating shell with a traversing hole having a known airflow resistance coefficient $K_S$.

41. The process of claim 25, further comprising the steps of:
calibrating the tube by:
connecting said second extremity of said tube to said blower of said apparatus,
connecting said first extremity to a calibrating shell with a traversing hole having a known airflow resistance coefficient $K_S$,
connecting said first pressure sensor to measure the first pressure at said first extremity of said tube,
switching the blower on,
instructing said control unit to measure the first and second pressures at said first pressure sensor and said second pressure sensor, said second pressure being measured at an outlet of said blower, and
calculating the value of the tube airflow resistance coefficient $K_T$ based on said measured first and second pressures and said known airflow resistance coefficient $K_S$.

* * * * *